(12) United States Patent
Mangiafico

(10) Patent No.: US 11,382,901 B2
(45) Date of Patent: Jul. 12, 2022

(54) TROPICAMIDE-BASED OPHTHALMIC FORMULATIONS

(71) Applicant: FOR HEALTH PHARMA S.R.L., Catania (IT)

(72) Inventor: Sebastiano Mangiafico, Catania (IT)

(73) Assignee: FOR HEALTH PHARMA S.R.L., Catania (IT)

( * ) Notice: Subject to any disclaimer, the term of this patent is extended or adjusted under 35 U.S.C. 154(b) by 32 days.

(21) Appl. No.: 16/625,480

(22) PCT Filed: Jun. 20, 2018

(86) PCT No.: PCT/IB2018/054546
§ 371 (c)(1),
(2) Date: Dec. 20, 2019

(87) PCT Pub. No.: WO2018/235015
PCT Pub. Date: Dec. 27, 2018

(65) Prior Publication Data
US 2021/0137900 A1 May 13, 2021

(30) Foreign Application Priority Data
Jun. 22, 2017 (IT) .................... 102017000069664

(51) Int. Cl.
| | | |
|---|---|---|
| *A61K 31/4409* | (2006.01) | |
| *A61K 9/08* | (2006.01) | |
| *A61K 47/02* | (2006.01) | |
| *A61K 47/14* | (2017.01) | |
| *A61K 47/40* | (2006.01) | |

(52) U.S. Cl.
CPC .......... *A61K 31/4409* (2013.01); *A61K 9/08* (2013.01); *A61K 47/02* (2013.01); *A61K 47/14* (2013.01); *A61K 47/40* (2013.01)

(58) Field of Classification Search
CPC .................................................. A61K 31/4409
USPC ....................................................... 514/357
See application file for complete search history.

(56) References Cited

U.S. PATENT DOCUMENTS 5,252,246 A   10/1993   Ding et al.

FOREIGN PATENT DOCUMENTS

| WO | WO 2015/031186 A1 | 3/2015 | |
| WO | WO 2015031186 | * 3/2015 | ............ A61K 31/00 |

OTHER PUBLICATIONS

Cappello, International Journal of Pharmaceutics, 2001, 213(1-2) 75-81.*
Abelson, M. et al., "Normal Human Tear pH by Direct Measurement", Arch Opthalmol, 99: 301 Feb. 1981).
Cappello, B. et al., "Solubilization of tropicamide by hydroxypropyl-β-cycodextrin and water-soluble polymers; in vitro/in vivo studies", International Journal of Pharmaceutics, 213: 75-81 (2001).
Carmignani, C. et al., "Ophthalmic Vehicles Containing Polymer-Solubilized Tropicamide: "In Vitro/In Vivo" Evaluation", Drug Development and Industrial Pharmacy, 28(1): 101-105 (2002).
Coles, W. et al., "Dynamics of ocular surface pH", British Journal of Ophthalmology, 68: 549-552 (1984).
Lee, V. et al., "Review: Topical Ocular Drug Delivery: Recent Developments and Future Challenges", Journal of Ocular Pharmacology, 2(1): 67-108 (1986).
Lim, L. et al., "Common eye drops and their implications for pH measurements in the management of chemical eye injuries", Int J. Ophthalmol, 7(6): 1067-1068 (Dec. 2014).
Saettone, M. et al., "Solubilization of tropicamide by poloxamers: physiochemical data and activity data in rabbits and humans", International Journal of Pharmaceutics, 43: 67-76 (1988).
International Search Report and Written Opinion of the International Searching Authority for International Patent Application No. PCT/IB2018/054546, dated Oct. 15, 2018, 11 pages.

* cited by examiner

*Primary Examiner* — Nizal S Chandrakumar
(74) *Attorney, Agent, or Firm* — Merchant & Gould P.C.

(57) ABSTRACT

An ophthalmic composition includes tropicamide, at least one cyclodextrin at concentrations of less than 2.5%, at least one surfactant at concentrations of less than 2.5%. The composition is physically stable at neutral pH.

10 Claims, No Drawings

TROPICAMIDE-BASED OPHTHALMIC FORMULATIONS

This application is a National Stage Application of PCT/IB2018/054546, filed 20 Jun. 2018, which claims the benefit of Ser. No. 102017000069664, filed 22 Jun. 2017 in Italy, and which applications are incorporated herein by reference. To the extent appropriate, a claim of priority is made to each of the above-disclosed applications.

The present invention relates to an ophthalmic composition comprising tropicamide, at least one cyclodextrin at concentrations of less than 2.5%, at least one surfactant at concentrations of less than 2.5%. Said composition is physically stable at neutral pH.

BACKGROUND ART

Tropicamide is a synthesis molecule with mydriatic and cycloplegic action used in ophthalmic formulations at concentrations typically from 0.5% to 1%. The main application is for diagnostic purposes, for the inspection of the fundus and other ocular structures. Therapeutic indications have been reported for cases of conjunctivitis, keratitis, iritis, iridocyclitis and uveitis.

Tropicamide (formula I)

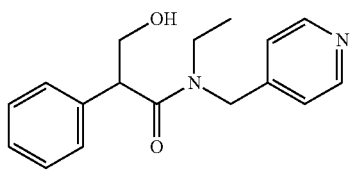

Formula (I)

is a weak base and the water solubility thereof is rather low and may decrease further in the presence of excipients such as buffers, osmotizing agents, preservatives, generally present in a formulation (Saettone et al., Int J Pharm 1988, 43; 67-76). The water-solubility of Tropicamide increases as pH decreases. 1% tropicamide solutions need a pH of about 5.

The physiological pH of the tear is variable in the range from 6.5 to 7.6, with an average value of 7.0±0.20 (Abelson M B, Arch Ophthalmol 1981, 99; 301). The administration of eye drops with a pH outside this range are poorly tolerated by the human eye, which reacts by inducing lacrimation to restore physiological pH. Induced lacrimation has, as an inevitable consequence, the lowering of the bioavailability of the active ingredient (Lee V H L et al., J Ocular Pharmacol 1986, 2; 67-108).

The currently available Tropicamide eye drops are formulated at acidic pHs from 4.0 to 5.8 (Lik Thai Lim et al., Int J Ophtalmol 2014, 7; 1067-1068) and should be administered in repeated doses, in some cases even 3-times at a distance of 5'. Such a type of administration causes a prolonged discomfort to the patient, since the eye irritated by acidic solutions takes from 20 to 40 minutes to restore its physiological pH (William H et al., British J Ophthalmol, 1984, 68; 549-552).

Cappello et al. (Int J Pharmaceutics 2001, 213; 75-81) describe the obtainment of a physically stable 1% Tropicamide solution at pH 7.4 in 0.02 M phosphate buffer: The physical stability is obtained by adding 4% hydroxypropyl-β-cyclodextrin (HP-β-CD). Although the concentration of HP-β-CD is not high, valid reasons including cost, toxicity and even bioavailability induce the same authors to reduce the HP-13-CD content. Cappello et al. report, in fact, that the concentration of HP-β-CD can be reduced from 4% to 0.9% with the association with 0.1% hydroxypropyl methylcellulose, heating the formulation in autoclave at 120° C. for 20 minutes, and then stirring the solution for 6 days at room temperature. It is apparent that the procedure, especially for the high temperatures required and the timing, is not industrially scalable.

Carmignani C et al. (Drug Development Industrial Pharmacy 2002, 28; 101-105, 2002) obtain a 1% TRP solution with surfactants. Four 1% TRP solutions are described, containing tyloxapol (TY), pluronic P85 (PL), Cremophor (CR) and associations of CR and PL, respectively. Of these 4 solutions, only the first 2 are formulated at neutral pH (7.0-7.2), while for the other two the pH does not exceed pH 6.2, therefore below the tolerability limit of the eye. With regard to surfactants, for TY there is a considerable in vitro toxicity on RAW 264.7 cells (murine macrophage-like) and on NIH/3T3 cells (murine fibroblasts). In general, TY toxicity is reduced by associating it with dipalmitoylphosphatidylcholine, which limits the interaction of TY with the cell membrane (Jung-Hua Steven Kuo Pharm Res 2006, 23). For PL, polymeric surfactants consisting of polyoxyethylene/polyoxypropylene co-polymer blocks, in varying proportions and of different molecular weight, the ophthalmological use is wide. 5,252,246 describes a relatively safe use of pluronic 85 up to 10%. In Carmignani et al., pluronic P85 is instead used at concentrations higher than 15%, which concentration is above the safety limits. Such a high percentage, 15% PL, required to solubilize 1% TRP at pH 7.2, is therefore poorly tolerated even at neutral pH.

The need to have an aqueous formulation based on Tropicamide with a neutral pH, well tolerated by the eye so as to obtain a longer pre-corneal residence time and therefore a greater bioavailability of the drug compared to that observed with the currently available compositions, is therefore strongly felt.

DESCRIPTION OF THE INVENTION

The present invention relates to a neutral pH composition comprising TRP from 0.1% to 1.2%, preferably from 0.2 to 1%, even more preferably from 0.4 to 0.8%, at least one cyclodextrin at concentrations lower than 2.5%, and at least one surfactant, at concentrations lower than 2.5%.

Said composition, formulated as described in the present invention, proved to be well tolerated when administered to the eye, as well as being physically stable for 24 months.

The following examples demonstrate how the two excipients cyclodextrin and surfactant, used in combination, surprisingly show a synergistic solubilizing effect such as to allow the reduction of the concentration of the volumes required when they are used individually. This means that the total content given by the sum of cyclodextrin and surfactant, required to keep tropicamide in solution at neutral pH, is lower than the required content of cyclodextrin or surfactant used individually.

The advantageous effects observed with the formulation according to the present invention are achieved by the synergy between cyclodextrin and a surfactant, where said surfactant consists of a compound other than a cyclodextrin.

The composition according to the present invention is formulated at room temperature, without requiring long times for the dissolution of tropicamide.

Said cyclodextrins are preferably γ- or β-cyclodextrins, even more preferably HP-β-CD. The concentration of HP-β-CD is from 0.5 to 2.5%, preferably from 0.8 to 2.0%.

Said surfactants are selected from the group comprising quaternary ammonium salts, hydrophilic non-ionic surfactants such as polyethylene glycol (15)-hydroxystearate (Solutol HS 15 SOL), polyethylene glycol (40). Preferably, said surfactant is polyethylene glycol (15)-hydroxystearate and is at a concentration ranging from 0.5 to 2.5%, preferably from 0.8 to 2.0%.

In order to obtain the neutral pH, the composition comprises a phosphate, citrate or borate buffer in a pH range from 6.5 to 7.4 and preferably from pH 6.8 to 7.2. For pH correction, strong acidic solutions or strong bases may be used.

Said composition, in one embodiment, comprises osmotizing agents preferably selected from the group comprising glycerol, sorbitol, mannitol, trehalose and sodium chloride.

Said composition, in one embodiment, also comprises viscous polymers preferably selected from the group comprising Carbopol, polyvinyl alcohol, hydroxypropyl cellulose, HP-Guar, dextran and hyaluronic acid, preferably sodium hyaluronate (HA) at concentrations from 0.01% to 0.25%, or from 0.08 to 0.2%.

Said composition, in one embodiment, also comprises preservatives, preferably selected from the group comprising ethylenediaminetetraacetic acid (EDTA), benzalkonium chloride or polyhexanide (PHMB).

The composition according to the present invention is exemplified in the following examples.

Examples 1-3: Formulations of TRP+HP-β-CD+SOL at Different TRP Concentration

| Ingredients | Example 1 % w/w | Example 2 % w/w | Example 3 % w/w |
|---|---|---|---|
| TRP | 0.5 | 1.0 | 0.2 |
| HP-β-CD | 1.0 | 2.0 | 0.5 |
| SOL | 1.5 | 2.5 | 0.8 |
| Sodium phosphate dibasic dodecahydrate | 0.2 | 0.2 | 0.2 |
| Sodium phosphate monobasic bihydrate | 0.065 | 0.065 | 0.065 |
| Glycerol | 0.9 | 0.9 | 0.9 |
| Mannitol | 2.0 | 2.0 | 2.0 |
| Sodium Hyaluronate | 0.15 | 0.15 | 0.15 |
| EDTA-Na$_2$*2H$_2$O | 0.025 | 0.025 | 0.025 |
| PHMB | 0.001 | 0.001 | 0.001 |
| Purified water | up to 100 g | up to 100 g | up to 100 g |

Examples 4-6: 1% TRP Formulations Comprising Me-β-CD, Sb-β-CD or γCD

| Ingredients | Example 4 % w/w | Example 5 % w/w | Example 6 % w/w |
|---|---|---|---|
| TRP | 1.0 | 1.0 | 1.0 |
| Methyl-β-cyclodextrin (Me-β-CD) | 1.5 | | |
| Sulphobutylether-cyclodextrin (Sb-β-CD) | | 2.0 | |
| γ-Cyclodextrin | | | 2.5 |
| SOL | 2.5 | 2.5 | 2.5 |
| Sodium phosphate dibasic dodecahydrate | 0.2 | 0.2 | 0.2 |
| Sodium phosphate monobasic bihydrate | 0.065 | 0.065 | 0.065 |
| Glycerol | 0.9 | 0.9 | 0.9 |
| Mannitol | 2.0 | 2.0 | 2.0 |
| Sodium Hyaluronate | 0.15 | 0.15 | 0.15 |
| EDTA-Na$_2$*2H$_2$O | 0.025 | 0.025 | 0.025 |
| PHMB | 0.001 | 0.001 | 0.001 |
| Purified water | up to 100 g | up to 100 g | up to 100 g |

Examples 7-9: 1% TRP Formulations Comprising Cremophor, Tween 80, Pluronic 85

| Ingredients | Example 7 % w/w | Example 8 % w/w | Example 9 % w/w |
|---|---|---|---|
| TRP | 1.0 | 1.0 | 1.0 |
| HP-β-CD | 2.0 | 2.0 | 2.5 |
| polyethoxylated castor oil (Cremophor) | 2.5 | | |
| Tween 80 | | 2.0 | |
| Pluronic P85 | | | 2.5 |
| Sodium phosphate dibasic dodecahydrate | 0.2 | 0.2 | 0.2 |
| Sodium phosphate monobasic bihydrate | 0.065 | 0.065 | 0.065 |
| Glycerol | 0.9 | 0.9 | 0.9 |
| Mannitol | 2.0 | 2.0 | 2.0 |
| Sodium Hyaluronate | 0.15 | 0.15 | 0.15 |
| EDTA-Na$_2$*2H$_2$O | 0.025 | 0.025 | 0.025 |
| PHMB | 0.001 | 0.001 | 0.001 |
| Purified water | up to 100 g | up to 100 g | up to 100 g |

Examples 10-14: 1% TRP Formulations Comprising Thickening Agents

| Ingredients | Example 10 % w/w | Example 11 % w/w | Example 12 % w/w | Example 13 % w/w | Example 14 % w/w |
|---|---|---|---|---|---|
| TRP | 1.0 | 1.0 | 1.0 | 1.0 | 1.0 |
| HP-β-CD | 2.0 | 2.0 | 2.0 | 2.0 | 2.0 |

-continued

| Ingredients | Example 10 % w/w | Example 11 % w/w | Example 12 % w/w | Example 13 % w/w | Example 14 % w/w |
|---|---|---|---|---|---|
| SOL | 2.5 | 2.5 | 2.5 | 2.5 | 2.5 |
| Sodium phosphate dibasic dodecahydrate | 0.2 | 0.2 | 0.2 | 0.2 | 0.2 |
| Sodium phosphate monobasic bihydrate | 0.065 | 0.065 | 0.065 | 0.065 | 0.065 |
| Glycerol | 0.9 | 0.9 | 0.9 | 0.9 | 0.9 |
| Mannitol | 2.0 | 2.0 | 2.0 | 2.0 | 2.0 |
| Hydroxypropyl methylcellulose | 0.4 | | | | |
| Carbopol | | 0.2 | | | |
| Polyvinyl alcohol | | | 0.5 | | |
| HP-Guar | | | | 1.0 | |
| Dextran | | | | | 5.0 |
| EDTA-Na$_2$*2H$_2$O | 0.025 | 0.025 | 0.025 | 0.025 | 0.025 |
| PHMB | 0.001 | 0.001 | 0.001 | 0.001 | 0.001 |
| Purified water | up to 100 g | up to 100 g | up to 100 g | up to 100 g | up to 100 g |

Examples 15-19 (Comparative): Formulations Similar to the Formulations of Examples 10-14 but which DO NOT Comprise Cyclodextrins

| Ingredients | Example 15 % w/w | Example 16 % w/w | Example 17 % w/w | Example 18 % w/w | Example 19 % w/w |
|---|---|---|---|---|---|
| TRP | 1.0 | 1.0 | 1.0 | 1.0 | 1.0 |
| SOL | 2.5 | 2.5 | 2.5 | 2.5 | 2.5 |
| Sodium phosphate dibasic dodecahydrate | 0.2 | 0.2 | 0.2 | 0.2 | 0.2 |
| Sodium phosphate monobasic bihydrate | 0.065 | 0.065 | 0.065 | 0.065 | 0.065 |
| Glycerol | 0.9 | 0.9 | 0.9 | 0.9 | 0.9 |
| Mannitol | 2.0 | 2.0 | 2.0 | 2.0 | 2.0 |
| Hydroxypropyl methylcellulose | 0.4 | | | | |
| Carbopol | | 0.2 | | | |
| Polyvinyl alcohol | | | 0.5 | | |
| HP-Guar | | | | 1.0 | |
| Dextran | | | | | 5.0 |
| EDTA-Na$_2$*2H$_2$O | 0.025 | 0.025 | 0.025 | 0.025 | 0.025 |
| PHMB | 0.001 | 0.001 | 0.001 | 0.001 | 0.001 |
| Purified water | up to 100 g | up to 100 g | up to 100 g | up to 100 g | up to 100 g |

Examples 20-22 (Comparative): Formulations Similar to the Formulations of Examples 7-9 but which DO NOT Comprise a Surfactant

| Ingredients | Example 20 % w/w | Example 21 % w/w | Example 22 % w/w |
|---|---|---|---|
| TRP | 1.0 | 1.0 | 1.0 |
| HP-β-CD | 2.0 | 2.0 | 2.5 |
| Sodium phosphate dibasic dodecahydrate | 0.2 | 0.2 | 0.2 |
| Sodium phosphate monobasic bihydrate | 0.065 | 0.065 | 0.065 |
| Glycerol | 0.9 | 0.9 | 0.9 |
| Mannitol | 2.0 | 2.0 | 2.0 |
| Sodium Hyaluronate | 0.15 | 0.15 | 0.15 |
| EDTA-Na$_2$*2H$_2$O | 0.025 | 0.025 | 0.025 |
| PHMB | 0.001 | 0.001 | 0.001 |
| Purified water | up to 100 g | up to 100 g | up to 100 g |

Examples 23-24 (Comparative): Formulations Similar to the Formulations of Examples 1-2 but which DO NOT Comprise a Surfactant

| Ingredients | Example 23 % w/w | Example 24 % w/w |
|---|---|---|
| TRP | 0.5 | 1.0 |
| HP-β-CD | 1.0 | 2.0 |
| Sodium phosphate dibasic dodecahydrate | 0.2 | 0.2 |
| Sodium phosphate monobasic bihydrate | 0.065 | 0.065 |
| Glycerol | 0.9 | 0.9 |
| Mannitol | 2.0 | 2.0 |
| Sodium Hyaluronate | 0.15 | 0.15 |
| EDTA-Na$_2$*2H$_2$O | 0.025 | 0.025 |
| PHMB | 0.001 | 0.001 |
| Purified water | up to 100 g | up to 100 g |

Below are given the stability studies related to the formulations of Examples 1 to 24.

It should be noted that, as for the comparative Examples 15 to 24, the same studies could not be conducted because the TRP in said formulations did not go into solution when operating at 25° C. or, within one month from preparation, the formation of a precipitate occurred.

Conversely, for the formulations comprising the components according to the present invention, the following data were obtained.

Stability of the formulations of Examples 1-5 at a temperature of 25±2° C.

| Months | | Example 1 | Example 2 | Example 3 | Example 4 | Example 5 |
|---|---|---|---|---|---|---|
| Initial value | % TRP | 0.5 | 1.0 | 0.2 | 1.0 | 1.0 |
| | pH | 7.0 | 7.0 | 7.1 | 7.0 | 7.0 |
| | mOsm/kg | 285 | 290 | 283 | 268 | 288 |

-continued

|   |        | Example 1 | Example 2 | Example 3 | Example 4 | Example 5 |
|---|--------|-----------|-----------|-----------|-----------|-----------|
| 3 | % TRP  | 0.5       | 1.0       | 0.2       | 1.0       | 1.0       |
|   | pH     | 7.0       | 7.0       | 7.1       | 7.0       | 7.0       |
|   | mOsm/kg| 287       | 292       | 285       | 291       | 290       |
| 12| % TRP  | 0.5       | 1.0       | 0.2       | 1.0       | 1.0       |
|   | pH     | 7.0       | 6.9       | 7.1       | 7.0       | 6.9       |
|   | mOsm/kg| 288       | 295       | 288       | 295       | 294       |
| 18| % TRP  | 0.5       | 1.0       | 0.2       | 1.0       | 1.0       |
|   | pH     | 7.0       | 6.9       | 7.0       | 6.9       | 6.9       |
|   | mOsm/kg| 292       | 298       | 293       | 298       | 298       |
| 24| % TRP  | 0.5       | 1.0       | 0.2       | 1.0       | 1.0       |
|   | pH     | 6.9       | 6.8       | 7.0       | 6.9       | 6.8       |
|   | mOsm/kg| 295       | 301       | 295       | 302       | 300       |

Stability of the formulations of Examples 6-10 at a temperature of 25±2° C.

|        |              |         | Example 6 | Example 7 | Example 8 | Example 9 | Example 10 |
|--------|--------------|---------|-----------|-----------|-----------|-----------|------------|
| Months | Initial value| % TRP   | 1.0       | 1.0       | 1.0       | 1.0       | 1.0        |
|        |              | pH      | 7.0       | 7.1       | 7.1       | 7.0       | 7.1        |
|        |              | mOsm/kg | 290       | 289       | 290       | 288       | 291        |
|        | 3            | % TRP   | 1.0       | 1.0       | 1.0       | 1.0       | 1.0        |
|        |              | pH      | 7.0       | 7.1       | 7.0       | 7.0       | 7.1        |
|        |              | mOsm/kg | 293       | 292       | 293       | 290       | 291        |
|        | 12           | % TRP   | 1.0       | 1.0       | 1.0       | 1.0       | 1.0        |
|        |              | pH      | 6.9       | 7.1       | 7.0       | 6.9       | 7.0        |
|        |              | mOsm/kg | 296       | 295       | 296       | 293       | 293        |
|        | 18           | % TRP   | 1.0       | 1.0       | 1.0       | 1.0       | 1.0        |
|        |              | pH      | 6.9       | 7.1       | 7.0       | 6.9       | 7.0        |
|        |              | mOsm/kg | 298       | 302       | 300       | 294       | 295        |
|        | 24           | % TRP   | 0.9       | 1.0       | 0.9       | 1.0       | 1.0        |
|        |              | pH      | 6.8       | 6.9       | 6.9       | 6.9       | 6.9        |
|        |              | mOsm/kg | 301       | 303       | 302       | 298       | 301        |

The compositions of Examples 11-14 comprise TRP, HP-β-CD and Solutol at the same concentrations included in the composition according to Example 2 and Example 10, the difference being the presence of thickening agents. The stability data obtained are superimposable with the data obtained in the absence of thickening agents, confirming that the stabilization effect is obtained due to the synergistic effect of cyclodextrins and surfactant and it is not affected by the addition of thickening agents.

The invention claimed is:

1. An ophthalmic composition comprising tropicamide at concentrations of 0.1% to 1.2%, at least one cyclodextrin, wherein said at least one cyclodextrin is hydroxypropyl-β-cyclodextrin (HP-β-CD) at concentrations of 0.8% to 2.0%, at least one surfactant, wherein said at least one surfactant is polyethylene glycol (15)-hydroxystearate at concentrations of 0.8% to 2.0%.

2. A composition according to claim 1, wherein said at least one surfactant is selected from a group which does not comprise cyclodextrins.

3. A composition according to claim 1, comprising a phosphate, citrate or borate buffer and is in a pH range from 6.5 to 7.4.

4. A composition according to claim 1, further comprising osmotizing agents and/or thickening polymers and/or preservatives.

5. A pharmaceutical formulation which is eye drops comprising the composition according to claim 1 and pharmaceutically acceptable excipients.

6. A method for inspection of the fundus and other ocular structures, in therapeutic treatment of conjunctivitis, keratitis, iritis, iridocyclitis and/or uveitis comprising administration of a composition according to claim 5 to a patient in need thereof.

7. A composition according to claim 1, wherein said tropicamide is at concentrations from 0.2% to 1%.

8. A composition according to claim 1, wherein said tropicamide is at concentrations from 0.4% to 0.8%.

9. A composition according to claim 1, comprising a phosphate, citrate or borate buffer and is in a pH range from pH 6.8 to pH 7.2.

10. A composition according to claim 1, the composition being adapted for inspection of the fundus of the eye and other ocular structures, in therapeutic treatment of conjunctivitis, keratitis, iritis, iridocyclitis and/or uveitis.

* * * * *